United States Patent [19]

Zmijewski, Jr. et al.

[11] Patent Number: 5,057,607
[45] Date of Patent: Oct. 15, 1991

[54] ENANTIOMERICALLY SELECTIVE BIOCATALYZED ACYLATION

[75] Inventors: Milton J. Zmijewski, Jr., Carmel; Jeffrey N. Levy, Lafayette, both of Ind.

[73] Assignee: Eli Lilly and Company, Indianapolis, Ind.

[21] Appl. No.: 591,586

[22] Filed: Oct. 2, 1990

Related U.S. Application Data

[63] Continuation-in-part of Ser. No. 535,086, Jun. 8, 1990, abandoned.

[51] Int. Cl.$^5$ ............... C07D 205/085; C12P 17/16; C07B 43/06
[52] U.S. Cl. ..................... 540/364; 435/129
[58] Field of Search ............... 540/364; 435/129

[56] References Cited

U.S. PATENT DOCUMENTS

| | | | |
|---|---|---|---|
| 3,150,059 | 9/1964 | Kleinschmidt et al. | 195/36 |
| 4,316,958 | 2/1982 | Hirata et al. | 435/119 |
| 4,332,896 | 6/1982 | Hashimoto et al. | 435/119 |
| 4,335,211 | 6/1982 | Hashimoto et al. | 435/119 |
| 4,389,488 | 6/1983 | Grabley | 435/106 |
| 4,859,602 | 8/1989 | Zimmerman | 435/128 |

FOREIGN PATENT DOCUMENTS

| | | |
|---|---|---|
| 319471 | 6/1989 | European Pat. Off. |
| 1369462 | 9/1974 | United Kingdom |

OTHER PUBLICATIONS

M. Cole, J. Biochem (1969) 115, p. 741.
Kaufmann et al., Proceeding of the Conference on Antimicrobial Agents, 1960 p. 1–5.
Bondareva et al., Biokhimiya, vol. 34, No. 3, pp. 478–482 (1969).
J. G. Shwalae et al., Process Biochem., 24 (4) p. 146 (1989).

*Primary Examiner*—Mark L. Berch
*Attorney, Agent, or Firm*—William C. Martens; Leroy Whitaker

[57] ABSTRACT

An enantiomerically selective process for acylating racemic 3-amino azetidinone intermediates is provided using penicillin G amidase(acylase) as biocatalyst.

10 Claims, No Drawings

ENANTIOMERICALLY SELECTIVE BIOCATALYZED ACYLATION

CROSS-REFERENCE

This application is a continuation-in-part of application Ser. No. 07/535,086 filed June 8, 1990, abandoned.

BACKGROUND OF THE INVENTION

An important clinical trial candidate, (6R,7S) 7-(R)-phenylglycylamido-3-chloro-1-azabicyclo[4.2.0]-oct-2-ene-8-one-2-carboxylic acid (loracarbef), claimed in U.S. Pat. No. 4,708,956, may be synthesized by various routes. One of the more noteworthy total syntheses of loracarbef is that made possible by Evans and Sjogren, U.S. Pat. No. 4,665,171. The Evans and Sjogren methodology provides a chiral 2+2 (ketene plus imine) cycloaddition, and accordingly, entry to a wide variety of chiral cis β-lactams. However, the Evans and Sjogren methodology requires the utilization of a chiral auxiliary of the formula

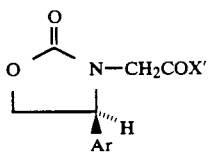

in the 2+2 cycloaddition with a Schiff's base, wherein X' is chloro, bromo, trifluoroacetoxy, or OP(=)X$_2$, wherein X is halogen. The above chiral auxiliary can be synthesized in seven steps from L-phenylglycine. The resulting cycloaddition provides compounds of the formula

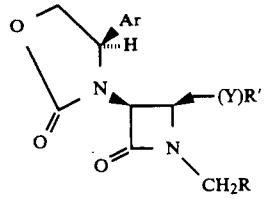

wherein Ar is phenyl, $C_1$-$C_4$ alkylphenyl, halophenyl, $C_1$-$C_4$ alkoxyphenyl, naphthyl, thienyl, furyl, benzoenyl, or benzofuryl; R is phenyl, $C_1$-$C_4$ alkylphenyl, $C_1$-$C_4$ alkoxyphenyl, or halophenyl; Y is —CH=CH—, or —CH$_2$-CH$_2$-; and R' is phenyl, $C_1$-$C_4$ alkylphenyl, $C_1$-$C_4$ alkoxyphenyl, halophenyl, furyl or naphthyl.

The obvious shortcomings of the Evans and Sjogren route are that a very expensive starting material, L-phenylglycine(when Ar is phenyl), is used, the chiral auxiliary is synthesized in several steps in linear fashion; and further, the chiral auxiliary is removed and discarded using Li/NH$_3$/t-C$_4$H$_9$OH to provide a free 3-amino-azetidinone.

As an achiral alternative, Hatanaka et al., *Tetrahedron Letters*, Vol. 24, No. 49, pp. 4837-4838 (1983), provides a method for preparing a 3-hydroxy(±)1-carbacephalosporin via a 2+2 cycloaddition much in the same fashion as that of Evans and Sjogren, but with azidoacetyl chloride rather than a chiral auxiliary as the ketene source. The Hatanaka methodology provides many of the same intermediates as does the Evans and Sjogren synthesis, albeit in achiral form. The advantage of the achiral synthesis of Hatanaka is economy of steps and starting material. However, an achiral strategy necessitates a resolution of the cis-racemic β-lactam at some point during the synthesis because a chiral (ββ)system is ultimately desired.

SUMMARY OF THE INVENTION

Cis (racemic at 2 and 3 positions) 3-amino2-[2-(2-furanyl)ethyl]-4-oxo-1-azetidine acetic acid (or acetic acid, $C_1$-$C_4$ alkyl ester) is resolved by the practice of this invention. The cis ββ enantiomer, i.e., (2R,3S)-3-amino-2-[2-(2-furanyl)ethyl]-4-oxo-1-azetidine acetic acid(or acetic acid, $C_1$-$C_4$ alkyl ester) can be selectively acylated with an ester of a desired acyl substituent such as methyl phenylacetate or methyl phenoxyacetate in the presence of a penicillin G amidase enzyme as biocatalyst. If the desired acyl substituent is phenylacetyl, phenylacetic acid may also be utilized. The reaction thus provides the cis ββ(2,3)-3-acylamino enantiomer, a useful intermediate in the total synthesis of 1-carba (dethia)-3-cephems, in high enantiomeric purity, by providing a method for selectively acylating the ββ enantiomer; the αα enantiomer remains substantially in free 3-amino form. The desired acylated product can then be isolated by precipitation from solution or by isolation using known extraction and/or chromatography techniques from the 3-amino azetidinone (in αα configuration).

DETAILED DESCRIPTION OF THE INVENTION

The present invention provides a process for preparing a compound of Formula (1)

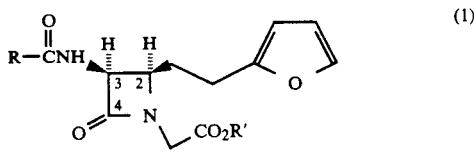

wherein R is

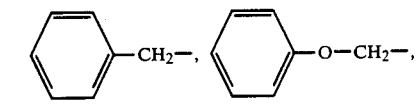

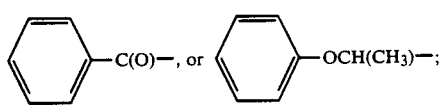

and R' is hydrogen or a $C_1$-$C_4$ alkyl group; which comprises reacting a cis(2,3) racemic mixture of Formula (2)

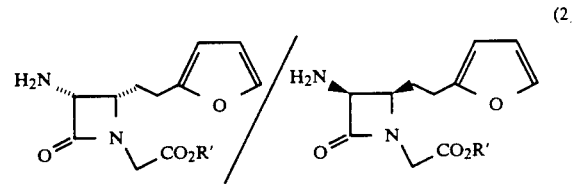

where R' is as defined above, with a compound of the

wherein R is as defined above, and R" is $C_1$-$R_4$ alkyl, or hydrogen, provided that when R" is hydrogen, R is

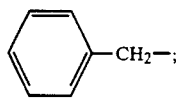

in the presence of a penicillin G amidase enzyme.

In the above process, the term $C_1$-$C_4$ alkyl refers to methyl, ethyl, propyl, butyl, isopropyl, isobutyl, and t-butyl. Methyl is preferred.

Preferred compounds of the formula RC(O)-OR" which can be used in the present invention include methyl phenylacetate, methyl phenoxyacetate, methyl benzoylformate, and methyl (phenoxy)(methyl)acetate. The process of the present invention wherein R is phenoxy is preferred. In this regard, methyl phenoxyacetate is an especially preferred compound of the formula RC(O)-OR".

In the above process, the racemic mixture (2), denoted as the substrate for the reaction, can be obtained by methodology known in the β-lactam art. For example, a 2+2 cycloaddition reaction as set forth in Scheme 1 may be utilized:

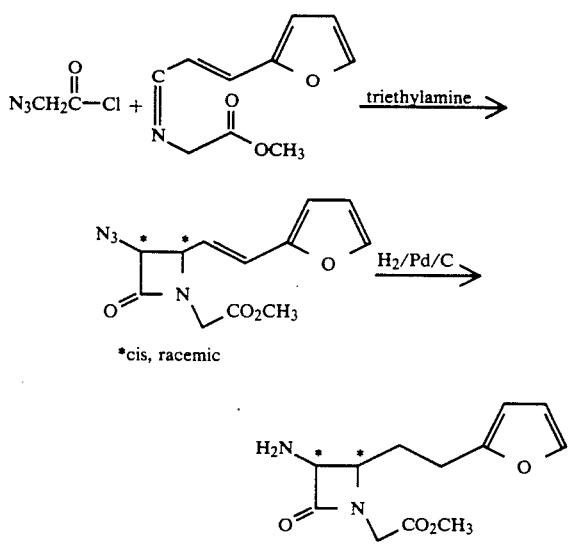

The ketene and imine (2+2) cycloaddition reaction may be performed by the procedure of Hatanaka, et al., Tetrahedron Letters, Vol. 24, No. 44, pp. 4837-4838 (1983). The subsequent catalytic hydrogenation be carried out using known methodology, e. g., $H_2$/Pd/C.

The term "penicillin G amidase" (or the alternative term "penicillin G acylase") is well-known in the β-lactam art as an enzyme which catalyzes the hydrolysis of the penicillin G sidechain (phenylacetyl) from penicillin substrates. Penicillin G amidases suitable for use in the process of the present invention may be isolated by known methodology from many organisms, for example, E. coli, B. megaterium, Ps. melanogenum, K. citrophila, and P. rettgei. In this regard Schlwale and Sivarawan, Process Biochemistry, Aug., 1989, pp. 146-154 sets forth a review of the state of the art of penicillin G amidase (acylase) production and application. Penicillin G amidase isolated from E. coli is preferred.

Once isolated, the penicillin G amidase may be used in "free" form, i.e., solubilized in aqueous or substantially aqueous solutions, or may be immobilized onto a support matrix such as an intermolecular adduct with glutaraldehyde; Sepharoses; Sephadex G-200 TM, acrylamide, N, N-methylenebis (acrylamide) and maleic anhydride; Dextran TM ; maleic anhydride; tetramethylene glycol; dimethacrylate; methacrylic acid, DEAE-Cellulose TM ; CM-Cellulose TM ; AE-Cellulose TM ; and other cellulose derivatives; CM-Sephadex Amberlite IRC-50 TM and other weak cation and anion exchangers; ethylene maleic anhydride copolymers; Nylon TM ; Amberlite XAD-7 TM ; Sucrose/epichlorohydrin copolymer; polyacrylamide; cellulose; intermolecular adduct with glutaraldehyde; acrylamide copolymer; anion exchange phenol-formaldehyde resin; DEAE-Sephadex TM ; glycidyl methacrylate; methylene bisacrylamide; diatomaceous earth; poly(hydroxyethylmethacrylate); Eupergit C TM ;basic anion exchanger (polyamine; styrene; divinyl benzene); cellulose triacetate fibres; AH-Sepharose TM /benzoquinone; nitrocellulose fibres; a polyethylene imine; Bentonite TM ; a polyacrylamide gel entrapment or derivatised polyacrylonitrile.

The immobilized penicillin G amidase may be obtained commercially. For example, the immobilized enzyme used in the experimental section below was obtained from SCLAVO S.p.A. - Biochemical Division De. Bi., S.S. Podana Superiore, Km. 160,20060 - Cassina de Pecchi - Milan, Italy. It is believed that any penicillin G amidase enzyme will be efficacious as a biocatalyst in the present invention whether used in free form or immobilized on a support matrix; however, it is preferred that the enzyme be immobilized on a solid support matrix, because such catalysts can be used several times. For example, when the reaction is deemed complete, the immobilized enzyme may simply be filtered away from the reaction mixture, washed with deionized water, stored in glycerol/water under an inert atmosphere such as nitrogen or argon at reduced temperature, for example at about 4° C., and re-used.

The substrate of Formula (2) is preferably present in the reaction mixture in a concentration of 0.1% (w/w) to about 20%(w/w) although concentration is not critical to the operability of the process. The amount of penicillin G amidase present in the reaction mixture dictates the rate of reaction, because it serves as a biocatalyst. A concentration of from about 10 I.U./g substrate (i.e., the β-lactam of formula (2)), to about 125 I.U./g substrate of penicillin G amidase is preferred. More preferably, the concentration will be at the lower end of the foregoing range, i.e., from about 10 I.U./g substrate to about 30 I.U./g substrate, and, most preferably, from about 15 I.U./g substrate to about 25 I.U./g. In the context it is used herein, one international unit (I.U.) is the amount of enzyme that will catalyze hydrolysis of one micromole of penicillin G in one minute at 28° C.

The acylation reaction of the present invention may be carried out in aqueous media at a pH of about 5 to about 8, preferably at about pH=6, thus providing an environmentally-compatible synthesis of intermediates useful in the synthesis of 1-carba(dethia)3-cephems which is suitable for use in large scale synthesis. Alternatively, the reaction may be carried out in a water/water-miscible polar organic solvent mixture comprising from about 1 to about 28% of a polar organic solvent such as acetone, tetrahydrofuran, propylene glycol methyl ether, propylene glycol, ethylene glycol dimethyl ether, 2-methoxyethyl ether, ethylene glycol, or glycerol, and from about 99% to about 72% water.

The temperature at which the process may be carried out will be appreciated by one of ordinary skill in enzyme catalysis and thus is not a critical limitation of the process; however, a temperature range of about 10° C. to about 45° C. is preferred. A more highly preferred temperature is about 28° C.

Once acylated, the compound of Formula 1 may be esterified(when R' is hydrogen), for example, with p-nitrobenzyl bromide to provide (2R,3S)-3-acylamino2-[2-(2-furanyl)ethyl]-4-oxo-1-azetidine acetic acid, p-nitrobenzyl ester, which can then be subjected to ozonolysis to provide the corresponding 2-[2-(carboxy)-eth-1-yl]derivative, which can then be derivatized to useful 1-carba(dethia) cephems. Copending application U.S. Ser. No. 07/405,602, incorporated herein by reference, teaches the conversion of this 4-carboxy azetidinone derivative to the corresponding 4-(2-phenoxycarbonyleth-1-yl) compound and subsequent cyclization to a 1-carba(dethia)-3-enol-3-cephem under Dieckmann cyclization conditions. The resulting 1-carba(dethia)-3-enol-3-cephem intermediate can then be chlorinated with triphenylphosphite dichloride using the method of Hatfield, U.S. Pat. No. 4,230,644, incorporated herein by reference, and acylated with an activated form of D-phenylglycine to provide the antibiotic loracarbef. See also, Bodurow et al., Tetrahedron Letters, 2321 30, 1989.

The following experimental section further illustrates the process provided by the present invention but in no way is intended to limit the scope thereof.

Experimental Section

EXAMPLE 1

(2R,3S)-3-Phenylacetylamino-2-[(2-furanyl)ethyl]-4-oxo-1-azetidine acetic acid, methyl ester A 100 mg sample of cis(racemic at 2 and 3 position) 3-amino-2-[2-(2-furanyl)ethyl]-4-oxo-1-azetidine acetic acid, methyl ester oxalate and 121 mg of methyl phenylacetate was added to 0.1 M potassium phosphate buffer(100ml) at pH=6.0, and the temperature maintained at 28° C. Milli-Q TM H$_2$O washed Sclavo penicillin G amidase (0.035 I.U./%mole of substrate; 0.100 I.U./mg of substrate) was added and the reaction allowed to proceed overnight. The reaction mixture was then extracted two times with ethyl acetate and dried over anhydrous sodium sulfate. The ethyl acetate portion was evaporated to dryness in vacuo and the residue was purified by column chromatography using a Kiesegel 60 TM column eluted with toluene/ethyl acetate (50/50), to obtain 45.7 mg (42.2% yield) of the title compound.

Elemental analysis: Calc.: C, 64.85; H, 5.99; N, 7.56; Found: C, 65.01; H, 5.88; N, 7.39.

Enantiomeric Excess=82.4% (as determined by chiral support liquid chromatography, i.e., a Chiracel OJ TM column, 30% isopropanol/70% hexane at 1.5 ml/min. Detection of the product occurs at 220 nm).

EXAMPLE 2

(2R,3S)-3-Phenoxyacetylamino-2-[(2-furanyl)ethyl]-4-oxo-1-azetidine acetic acid, methyl ester A 100 mg sample of [(2R,3S),(2S,3R)]-3-amino- <2-[2-(2-furanyl)ethyl]-4-oxo-1-azetidine acetic acid, methyl ester oxalate salt and a 135 mg sample of methyl phenoxyacetate were added to 0.1M phosphate buffer (100 ml final volume) and adjusted to pH=6.0 with 1N KOH. Milli-Q TM H$_2$O washed Sclavo penicillin G amidase (40 I.U. of enzyme per gram of substrate) was then added to the reaction mixture and the pH of reaction mixture was maintained at 6.0 and temperature at 28° C. for 8 hours. The reaction mixture was then filtered to remove the immobilized enzyme and extracted two times with ethyl acetate. The organic extracts were then dried over anhydrous sodium sulfate and concentrated to dryness in vacuo. The title compound was then isolated by column chromatography from this residue using a Kiesegel 60 TM column eluted with toluene/ethyl acetate (70/30). Yield: 13%.

Elemental Analysis: (assumes ½ molar equivalent of water) Calc.: C, 60.75; H, 5.86; N, 7.08; Found C, 61.28; H, 5.95; N, 6.82.

Enantiomeric Excess (as determined by chiral support chromatography as in Example 1)=97%

EXAMPLE 3

(2R,3S)-3-Phenoxyacetylamino-2-[2-(2-furanyl)ethyl]-4-oxo-1-azetidine acetic acid A 10% solution of [(2R,3S),(2S,3R)]-3-amino-2-[2-(2-furanyl)ethyl]-4-oxo-1-azetidine acetic acid (0.42 mmole/ml; 0.1 g/ml) in deionized H$_2$O was obtained by 10 N NaOH hydrolysis of the corresponding methyl ester oxalate salt (4.0 g total of the free acid as determined by HPLC assay). The pH of this solution was adjusted to 6.0 using phosphoric acid (total final volume was 40 ml). A 2.24 gm sample of methyl phenoxyacetate was added and the pH adjusted to 6.0 with 5N NH$_4$OH. Milli-Q TM H$_2$O washed Sclavo penicillin G amidase (84 I.U. of enzyme per g of substrate) was added and the pH maintained at 6.0 with 5N NH$_4$OH and the temperature held at 28° C. The reaction was run for 3 h, the immobilized enzyme filtered off, and the reaction mixture extracted (at pH 6.0) once with methylene chloride. The organic layer was discarded. The pH of the aqueous layer was then adjusted to 2.0 with sulfuric acid, and extracted once with methylene chloride. This methylene chloride extract was then dried over anhydrous sodium sulfate and concentrated to dryness in vacuo. The title compound was then purified using high performance liquid chromatography (Rainin TM C18 column eluted with 30% acetonitrile/70% water with 0.2% trifluoroacetic acid). Yield: 43.7% based on in situ yield as determined by high performance liquid chromatography.

Elemental Analysis: (assumes ½ mole of water) Calc.: C, 58.4; H, 5.16; N, 7.17; Found: C, 59.0; H, 5.18; N, 7.27.

Enantiomeric Excess: 100%

EXAMPLE 4

(2R, 3S)-3-Phenylacetylamino-2-[(2-furanyl)ethyl]-4-oxo-1-azetidine acetic acid, methyl ester A 4.00 gram sample (11.7 mmoles) of cis(racemic at 2 and 3 position) 3-amino-2-2-(2-furanyl)ethyl]-4-oxo-1-azetidine acetic acid, methyl ester oxalate was dissolved in 40 ml. of deionized water by adjusting the pH to 7.0 with concentrated NH4OH. After readjusting the pH to 6.0 with phosphoric acid, 1.41 grams (9.36 mmoles) of methyl phenylacetate was added and the temperature was maintained at 28° C. Milli-Q water washed Sclavo penicillin G amidase (84 I.U./gram of substrate; 7.18 I.U./mmole of substrate) was added and the reaction was allowed to proceed for four hours. The pH of the reaction was maintained at 6.0 by the addition of 2.5 N NH4OH. The reaction mixture was then filtered through a ground glass filter and the beads were washed successively with methylene chloride and water to remove product. The filtrate and washes were combined and the aqueous layer was extracted several times with methylene chloride. The extract was dried with anhydrous sodium sulfate and evaporated to dryness in vacuo. The residue, which contained 1.78 grams (41.1% yield) of title compound, was purified by semi-preparative HPLC using Waters RCM 25×10 column containing two cartridges of prep Nova-Pak HRC18 with one prep guard Nova-Pak HRC18 eluted with 0.2% trifluoroacetic acid in water/acetonitrile (70/30), to obtain 1.25 grams (28.8% yield) of the title compound.

Elemental analysis: Calc.: C, 64.85; H, 5.99; N, 7.56; Found: C, 64.93; H, 6.14; N, 7.06.

Enantiomeric Excess=96.4% (as determined by chiral support liquid chromatography, i.e., a Regis Chiralcel OJ column, 30% isopropanol/70% hexane at 1.0 ml/min., UV absorption at 220 nm.)

EXAMPLE 5

(2R, 3S)-3-Phenoxyacetylamino-2-[(2-furanyl)ethyl]-4-oxo-1-azetidine acetic acid, methyl ester A 4.00 gram sample (11.7 mmoles) of cis(racemic at 2 and 3 position) 3-amino-2-[2-(2-furanyl)ethyl]-4-oxo-1-acetidine acetic acid, methyl ester oxalate was dissolved in 40 ml. of deionized water by adjusting the pH to 7.0 with concentrated NH4OH. After readjusting the pH to 6.0 with phosphoric acid, 1.56 grams (9.36 mmoles) of methyl phenoxyacetate was added and the temperature was maintained at 28° C. Milli-Q water washed Sclavo penicillin G amidase (84 I.U./gram of substrate; 7.18 I.U./mmole of substrate) was added and the reaction was allowed to proceed for three hours. The pH of the reaction was maintained at 6.0 by the addition of 2.5 N NH4OH. The reaction mixture was then filtered through a ground glass filter and the beads were washed successively with methylene chloride and water to remove product. The filtrate and washes were combined and the aqueous layer was extracted several times with methylene chloride. The extract was dried with anhydrous sodium sulfate and evaporated to dryness in vacuo. The residue, which contained 1.98 grams (43.8% yield) of title compound, was purified by semi-preparative HPLC using Waters RCM 25×10 column containing two cartidges of prep Nova-Pak HRC18 with one prep guard Nova-Pak HRC18 eluted with 0.2% trifluoroacetic acid in water/acetonitrile (70/30), to obtain 1.50 grams (33.1% yield) of the title compound.

Elemental Analysis: Calc.: C, 62.17; H, 5.74; N, 7.25; Found: C, 62.42; H, 5.64; N, 7.04.

Enantiomeric Excess=98.4% (as determined by chiral support liquid chromatography, i.e., a Regis Chiralcel OJ column, 30% isopropanol/70% hexane at 1.0 ml/min., UV absorption at 220 nm.)

EXAMPLE 6

(2R, 3S)-3-Phenoxyacetylamino-2-[2-(2-furanyl)ethyl]-4-oxo-1-azetidine acetic acid, p-nitrobenzyl ester A 10% solution of [(2R, 3S), (2S, 3R)]-3-amino-2-2-(2-furanyl)ethyl]-4-oxo-1-azetidine acetic acid (0.24 mmole/ml; 0.1 g/ml) in deionized H2O was obtained as follows: 34.23 g of the corresponding methyl ester oxalate salt and 40 ml 5 N NaOH were simultaneously added to 125 ml of water. Additional 5 N NaOH solution was added as required to maintain the pH between 10.5 and 11.0. When no more sodium hydroxide was required to maintain a constant pH for 30 minutes, the zwitterion solution was filtered (to remove sodium oxalate) and the precipitate washed with 50 ml of water. The filtrate and washings were combined, and the pH of this solution was adjusted to 6.5 using phosphoric acid. Water-washed Sclavo penicillin G amidase (19 I.U. of enzyme per g of substrate) was added followed by 11.68 g of methyl phenoxyacetate. The pH of the reaction was maintained at 6.5 with 5 N NH<OH and the temperature held at 28° C. The reaction was run for 10 hours, the immobilized enzyme filtered off, and the enzyme beads washed with approximately 25 ml of water. Yield: 48.7% based on in situ yield as determined by high performance liquid chromatography. The desired acid was isolated as a p-nitrobenzyl ester. High performance liquid chromatographic analysis of the crystalline product gave the following results: 94.8% potency, 0.19% total related substances, and 100% enantiomeric excess. Assay-corrected yield of ester: 22.28 g, 43.9%. A second, identical example gave an assay-corrected yield of 23.19 g, 44.7%. (98.2% potency, 0.16% total related substances, 100% enantiomeric excess).

I claim:

1. A process for preparing a compound of Formula (1)

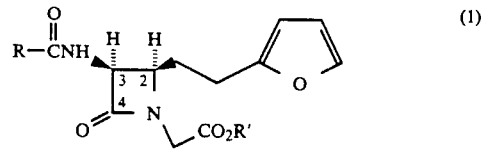

wherein R is

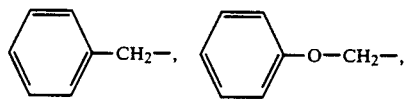

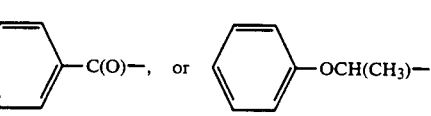

and R' is hydrogen or a C1-C4 alkyl group; which comprises reacting a cis (2,3) racemic mixture of Formula (2)

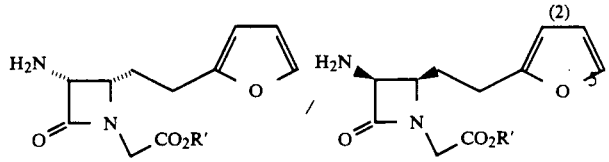

wherein R' is as defined above, with a compound of the formula

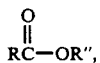

wherein R is as defined above, and R" is $C_1$-$C_4$ alkyl or hydrogen, provided that when R" is hydrogen, R is

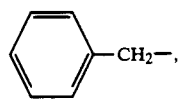

in the presence of a penicillin G amidase enzyme.

2. The process of claim 1, wherein R' is hydrogen.

3. The process of claim 1, wherein R' is methyl.

4. The process of claim 2 wherein R is

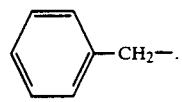

5. The process of claim 2 wherein R is

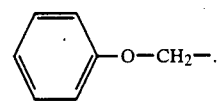

6. The process of claim 4, wherein the penicillin G amidase is derived from *E. coli*.

7. The process of claim 5, wherein the penicillin G amidase is derived from *E. coli*.

8. The process of claim 1 wherein the penicillin G amidase is immobilized on a solid support.

9. The process of claim 4 wherein the penicillin G amidase is immobilized on a solid support.

10. The process of claim 5, wherein the penicillin G amidase is immobilized on a solid support.

* * * * *